US012161302B2

(12) United States Patent
Oskin

(10) Patent No.: US 12,161,302 B2
(45) Date of Patent: *Dec. 10, 2024

(54) MEDICAL DEVICES FOR FLUID DELIVERY AND RELATED METHODS OF USE

(71) Applicant: Boston Scientific Scimed, Inc., Maple Grove, MN (US)

(72) Inventor: Christopher L. Oskin, Grafton, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 149 days.

This patent is subject to a terminal disclaimer.

(21) Appl. No.: 18/051,640

(22) Filed: Nov. 1, 2022

(65) Prior Publication Data

US 2023/0089491 A1    Mar. 23, 2023

Related U.S. Application Data

(63) Continuation of application No. 16/415,579, filed on May 17, 2019, now Pat. No. 11,517,191, which is a
(Continued)

(51) Int. Cl.
*A61B 1/12* (2006.01)
*A61B 1/00* (2006.01)
(Continued)

(52) U.S. Cl.
CPC ............ *A61B 1/126* (2013.01); *A61B 1/0002* (2013.01); *A61B 1/00059* (2013.01);
(Continued)

(58) Field of Classification Search
CPC ... A61B 1/126; A61B 1/0002; A61B 1/00066; A61B 1/00059; A61B 1/015
See application file for complete search history.

(56) References Cited

U.S. PATENT DOCUMENTS 4,567,880 A    2/1986  Goodman
4,822,344 A    4/1989  O'Boyle
(Continued)

FOREIGN PATENT DOCUMENTS

CN    1968639 A       5/2007
CN    101548873 A    10/2009
(Continued)

OTHER PUBLICATIONS

International Search Report and Written Opinion for International Application No. PCT/US2015/052287, mailed Dec. 23, 2015 (10 pages).

(Continued)

*Primary Examiner* — Nathan R Price
*Assistant Examiner* — John A Doubrava
(74) *Attorney, Agent, or Firm* — Bookoff McAndrews, PLLC

(57) ABSTRACT

A medical device may include an insertion portion longitudinally extending between a proximal end and a distal end. The insertion portion may define a channel extending therethrough. The medical device may further include a handle coupled to the proximal end of the insertion portion. The handle may further include an irrigation port in fluid communication with the channel and coupled to a source of irrigation fluid. Additionally, the handle may include an actuator and a pressurizer. Manipulation of the actuator may be configured to actuate the pressurizer to urge irrigation fluid distally through the channel.

20 Claims, 4 Drawing Sheets

Related U.S. Application Data continuation of application No. 14/865,725, filed on Sep. 25, 2015, now Pat. No. 10,335,020.

(60) Provisional application No. 62/056,313, filed on Sep. 26, 2014.

(51) Int. Cl.

| | | |
|---|---|---|
| *A61B 1/015* | (2006.01) | |
| *A61B 1/05* | (2006.01) | |
| *A61B 1/06* | (2006.01) | |
| *A61B 1/07* | (2006.01) | |
| *A61B 1/307* | (2006.01) | |

(52) U.S. Cl.
CPC ...... *A61B 1/00066* (2013.01); *A61B 1/00068* (2013.01); *A61B 1/015* (2013.01); *A61B 1/05* (2013.01); *A61B 1/0661* (2013.01); *A61B 1/0684* (2013.01); *A61B 1/07* (2013.01); *A61B 1/307* (2013.01)

(56) References Cited

U.S. PATENT DOCUMENTS

| | | | |
|---|---|---|---|
| 5,046,486 A | 9/1991 | Grulke et al. | |
| 5,271,379 A | 12/1993 | Phan et al. | |
| 5,322,500 A | 6/1994 | Johnson et al. | |
| 8,465,421 B2 | 6/2013 | Finkman et al. | |
| 10,335,020 B2 | 7/2019 | Oskin | |
| 11,517,191 B2* | 12/2022 | Oskin | A61B 1/307 |
| 2003/0032862 A1* | 2/2003 | Ota | A61B 1/015 |
| | | | 600/158 |
| 2005/0119527 A1 | 6/2005 | Banik et al. | |
| 2009/0281486 A1* | 11/2009 | Ducharme | A61M 5/16881 |
| | | | 604/147 |
| 2012/0006415 A1 | 1/2012 | Baur | |
| 2012/0006431 A1 | 1/2012 | Gilpatrick | |
| 2013/0072950 A1 | 3/2013 | Ross et al. | |
| 2013/0165758 A1* | 6/2013 | Young | A61D 7/00 |
| | | | 600/366 |
| 2013/0190561 A1 | 7/2013 | Oskin et al. | |

FOREIGN PATENT DOCUMENTS

| | | |
|---|---|---|
| EP | 2 106 735 A1 | 10/2009 |
| EP | 2572660 A2 | 3/2013 |
| JP | S57-164032 A | 10/1982 |
| JP | H06-189957 A | 7/1994 |
| JP | 2003-126026 A | 5/2003 |
| JP | 2004-000337 A | 1/2004 |
| JP | 2006-325814 A | 12/2006 |
| JP | 2008-028332 A | 2/2008 |
| JP | 2009-536552 A | 10/2009 |
| JP | 2011-010666 A | 1/2011 |
| JP | 2011-156217 A | 8/2011 |
| WO | 2012051697 A1 | 4/2012 |

OTHER PUBLICATIONS

Office Action in corresponding Japanese Application No. 2017-516345, dated Dec. 2, 2019 (3 pages).
Office Action in corresponding Japanese Application No. 2017-516345, dated Jul. 1, 2019 (2 pages).

* cited by examiner

MEDICAL DEVICES FOR FLUID DELIVERY AND RELATED METHODS OF USE

CROSS-REFERENCE TO RELATED APPLICATIONS

The application is a continuation of Ser. No. 16/415,579, filed May 17, 2019, which is a continuation application of U.S. application Ser. No. 14/865,725, filed Sep. 25, 2015, which claims the benefits of priority from U.S. Provisional Application No. 62/056,313, filed on Sep. 26, 2014, all of which are incorporated by reference in their entireties.

TECHNICAL FIELD

Embodiments of the present disclosure relate to medical systems and related methods for diagnosis and treatment. The medical systems and related methods may be used for ureteroscopy.

BACKGROUND

One challenge in diagnosing and treating internal areas of a subject's body has been adequately visualizing those internal areas. Visualization may be difficult to achieve in minimally invasive procedures, where elongated instruments with small diameters may be navigated through openings, passageways, and cavities of a subject's body, to access internal areas therein. Those elongated small-diameter instruments may include, for example, catheters or endoscopes.

Ureteroscopy is a procedure that may be performed to diagnose and treat urinary tract diseases and ureteral strictures. A ureteroscope may be inserted retrograde through the urinary tract to allow diagnosis and treatment of the urinary tract under visualization. During a ureteroscopy procedure, a viewing window, port, or lens of the ureteroscope may become obstructed with blood, tissue, fluids, and other materials within the body, or may become fogged over with condensation such that it prevents a medical professional from clearly viewing the body lumen and/or a medical tool extended through the ureteroscope. In addition, the area of interest within the body of the patient may become difficult to view due to blood and other debris that may collect within the area of interest. Further, the area of interest may be narrow and difficult to maneuver within. Dilation of the area of interest (e.g., via irrigation fluid) may be necessary to improve maneuverability within the area of interest.

In order to clean the lens, a medical professional may remove the ureteroscope from the body and manually wipe or otherwise remove debris or condensation. However, the need to withdraw the viewing ureteroscope from the patient, clean it, reinsert it, and reposition it, is highly inefficient and inconvenient. Alternatively, some ureteroscopes may be coupled with an irrigation supply line and a distal port to inject irrigation fluid across the lens to clear debris or condensation. If the medical professional determines there is a need to inject irrigation fluid, such as a need to clear the area of interest and/or a viewing lens of the ureteroscope or a need to dilate the area of interest, he or she is left to either remove one of his or her hands from the ureteroscope or the medical tool extending through the ureteroscope to actuate a fluid pump, or direct an assistant to actuate a fluid pump. However, removing one of their hands may result in losing a particular positioning of the ureteroscope and/or tool within the body and decrease procedural efficiency. On the other hand, if the medical professional opts to instruct an assistant to actuate a fluid pump, communication between the medical professional and assistant must be exact and clear, otherwise, the assistant may inadvertently inject too much or too little irrigation fluid, which may inhibit procedural efficiency.

The systems and methods of the current disclosure may rectify some of the deficiencies described above.

SUMMARY

Examples of the present disclosure relate to, among other things, medical systems and related methods for diagnosis and treatment. Each of the examples disclosed herein may include one or more of the features described in connection with any of the other disclosed examples.

In one example, a medical device may include an insertion portion longitudinally extending between a proximal end and a distal end. The insertion portion may define a channel extending therethrough. The medical device may further include a handle coupled to the proximal end of the insertion portion. The handle may further include an irrigation port in fluid communication with the channel and coupled to a source of irrigation fluid. Additionally, the handle may include an actuator and a pressurizer. Manipulation of the actuator may be configured to actuate the pressurizer to urge irrigation fluid distally through the channel. In other words, the actuator may be configured to control actuation of the pressurizer.

Examples of the medical device may additionally and/or alternatively include one or more of the following features: the handle may include a printed-circuit board housed within an interior of the handle; the pressurizer may be positioned on the printed circuit board; the pressurizer may be positioned externally of the printed circuit board; the handle may include at least two branches fluidly coupled to the channel; the irrigation port may be fluidly coupled to a first branch of the at least two branches and the pressurizer may be fluidly coupled to a second branch of the at least two branches; the pressurizer may be positioned upstream of the irrigation port; the pressurizer may include at least one of a piston pump and a peristaltic pump; the actuator may include at least one of a depressible trigger and a rotatable dial; the actuator may include a depressible trigger, wherein the actuator may be coupled to the pressurizer via a mechanical linkage; the actuator may include a rotatable dial, wherein the actuator may be coupled to a memory positioned on a printed circuit board within the handle; the memory may include stored commands for actuating the pressurizer; the actuator may include indicia representing at least one of a speed, a frequency, and/or a duration of desired irrigation fluid through the channel; and the irrigation source may include at least one of saline, water, medicament, and cleaning solution; a second port may be configured to receive a medical tool therethrough.

In another example, a medical device may include an insertion portion longitudinally extending between a proximal end and a distal end. The insertion portion may define a channel extending therethrough. The handle may be coupled to the proximal end of the insertion portion and the handle may include an irrigation port in fluid communication with the channel and coupled to a source of irrigation fluid. The handle may further include a rotatable actuator, a printed-circuit board housed within an interior of the handle, and a pressurizer housed within an interior of the handle. Manipulation of the actuator may be configured to actuate the pressurizer to urge irrigation fluid distally through the channel.

Examples of the medical device may additionally and/or alternatively include one or more of the following features: the handle may include at least two branches fluidly coupled to the channel; the irrigation port may be fluidly coupled to a first branch of the at least two branches and the pressurizer may be fluidly coupled to a second branch of the at least two branches; the pressurizer may be positioned upstream of the irrigation port; the actuator may include indicia representing at least one of a speed, a frequency, and/or a duration of desired irrigation fluid through the channel; the pressurizer may include at least one of a piston pump and a peristaltic pump; the actuator may be coupled to a memory positioned on a printed circuit board; and the memory may include stored commands for actuating the pressurizer.

In another example, a method using a medical device may include positioning an insertion portion of the medical device within the interior of a patient. The insertion portion may longitudinally extend between a proximal end and a distal end and define a channel extending therethrough. The method may also include manipulating an actuator on a handle of the medical device to actuate a pressurizer positioned within an interior of the handle. The handle may be coupled to the proximal end of the insertion portion and may include an irrigation port in fluid communication with the channel and coupled to a source of irrigation fluid. Further, the method may include urging irrigation fluid distally through the channel.

Examples of the method may additionally and/or alternatively include one or more of the following features: the handle may include at least two branches fluidly coupled to the channel; the irrigation port may be fluidly coupled to a first branch of the at least two branches and the pressurizer may be fluidly coupled to a second branch of the at least two branches; manipulating the actuator may include adjusting a speed, a frequency, and/or a duration of irrigation fluid through the channel; and the actuator includes at least one of a depressible trigger and a rotatable dial.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Overview

Embodiments of the present disclosure relate to a medical system for diagnosing and/or treating internal areas of a subject's body. The medical system may include a medical device having an incorporated pump for irrigation fluid.

Exemplary Embodiments

Reference will now be made in detail to exemplary embodiments of the present disclosure described above and illustrated in the accompanying drawings.

The terms "proximal" and "distal" are used herein to refer to the relative positions of the components of an exemplary medical device. When used herein, "proximal" refers to a position relatively closer to the exterior of the body or closer to a user using the medical device. In contrast, "distal" refers to a position relatively further away from the user using the medical device, or closer to the interior of the body.

Figure 1:
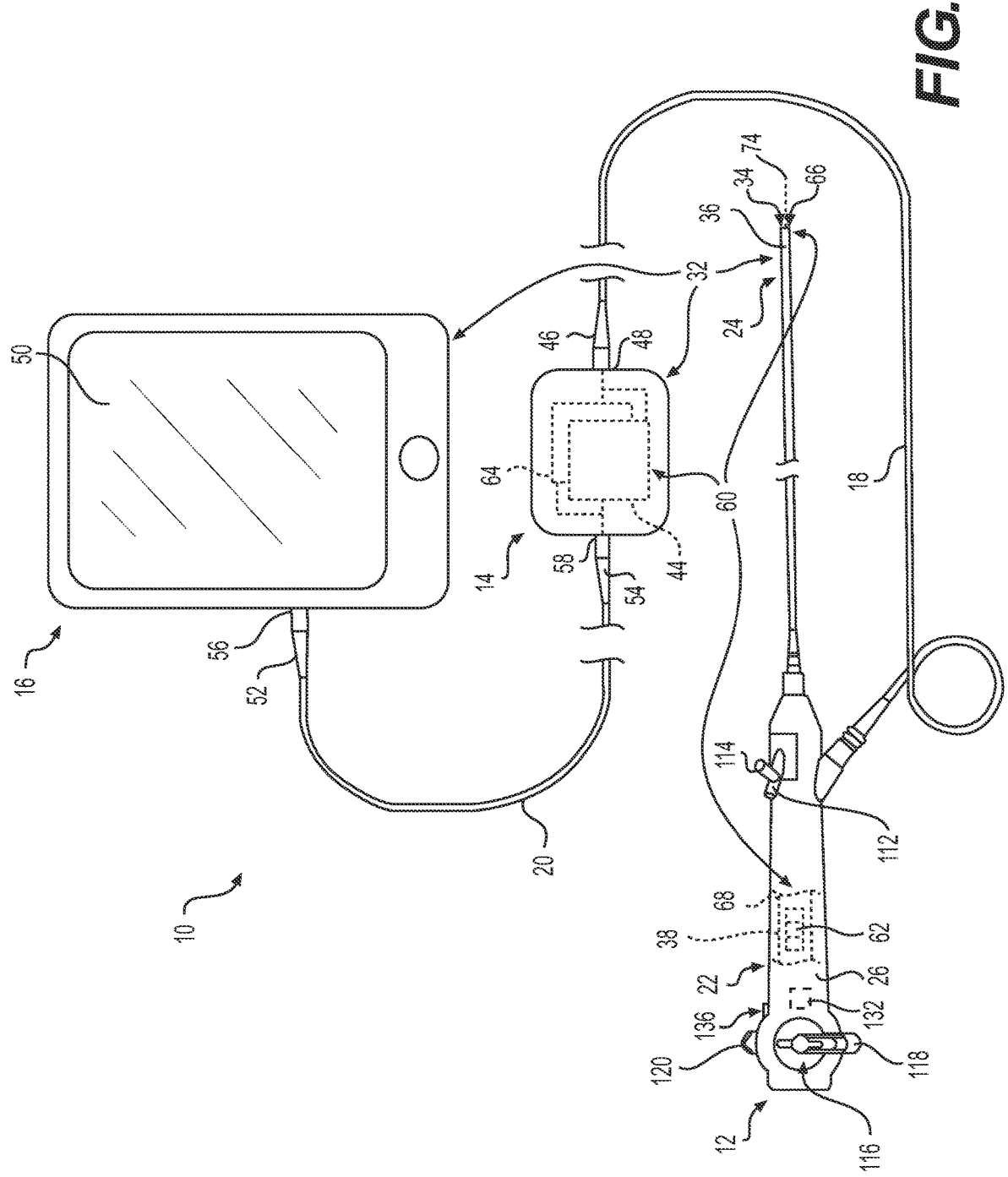
FIG. 1 illustrates an exemplary medical system in accordance with aspects of the present disclosure.

FIG. 1 shows an exemplary medical system 10. Medical system 10 may include a medical device 12, an interface box 14, and a computer 16. Medical device 12 may be coupled to interface box 14 by a distal connector 18. Computer 16 may be coupled to interface box 14 by a proximal connector 20.

Medical device 12 may include any device configured to allow a user to perform medical diagnoses and/or treatments on a subject. For example, medical device 12 may include any device configured to allow a user to access and view internal areas of a subject's body. Additionally or alternatively, medical device 12 may include any device configured to deliver medical instruments, such as, for example, biopsy forceps, graspers, baskets, snares, probes, scissors, retrieval devices, lasers, and/or other tools, into a subject's body. Medical device 12 may be inserted into a variety of body openings, lumens, and/or cavities. For example, medical device 12 may be inserted into any portion of a urinary tract, such as a ureter, a gastrointestinal lumen, such as an esophagus, a vascular lumen, and/or an airway.

According to aspects of the present disclosure, medical device 12 may be a ureteroscope. In some contemplated embodiments, medical device 12 may be a sterile, single-use, and disposable ureteroscope. Alternatively, medical device 12 may be a multiple-use, non-disposable ureteroscope. Other types of devices, however, may be substituted for the ureteroscope, including, as examples, an endoscope, a hysteroscope, a uteroscope, a bronchoscope, a cystoscope, and similar devices. Such devices may be single-use and disposable, or multiple-use and non-disposable.

Medical device 12 may include a handle assembly 22. Medical device 12 may also include an elongate tubular member 24 (e.g., insertion portion) operably connected to handle assembly 22. Tubular member 24 may include, for example, a catheter, and may be configured to be at least partially inserted into a subject's body and navigated to an internal area therein. Tubular member 24 may be flexible. For example, tubular member 24 may include one or more portions that are flexible. Its flexibility may allow tubular member 24 to be maneuvered into, through, and out of the subject's body. Tubular member 24 may be configured, for example, to traverse tortuous anatomical lumens of the subject's body. Tubular member 24 may be uniformly flexible, or may include a plurality of portions having varying degrees of flexibility or rigidity.

Figure 2:
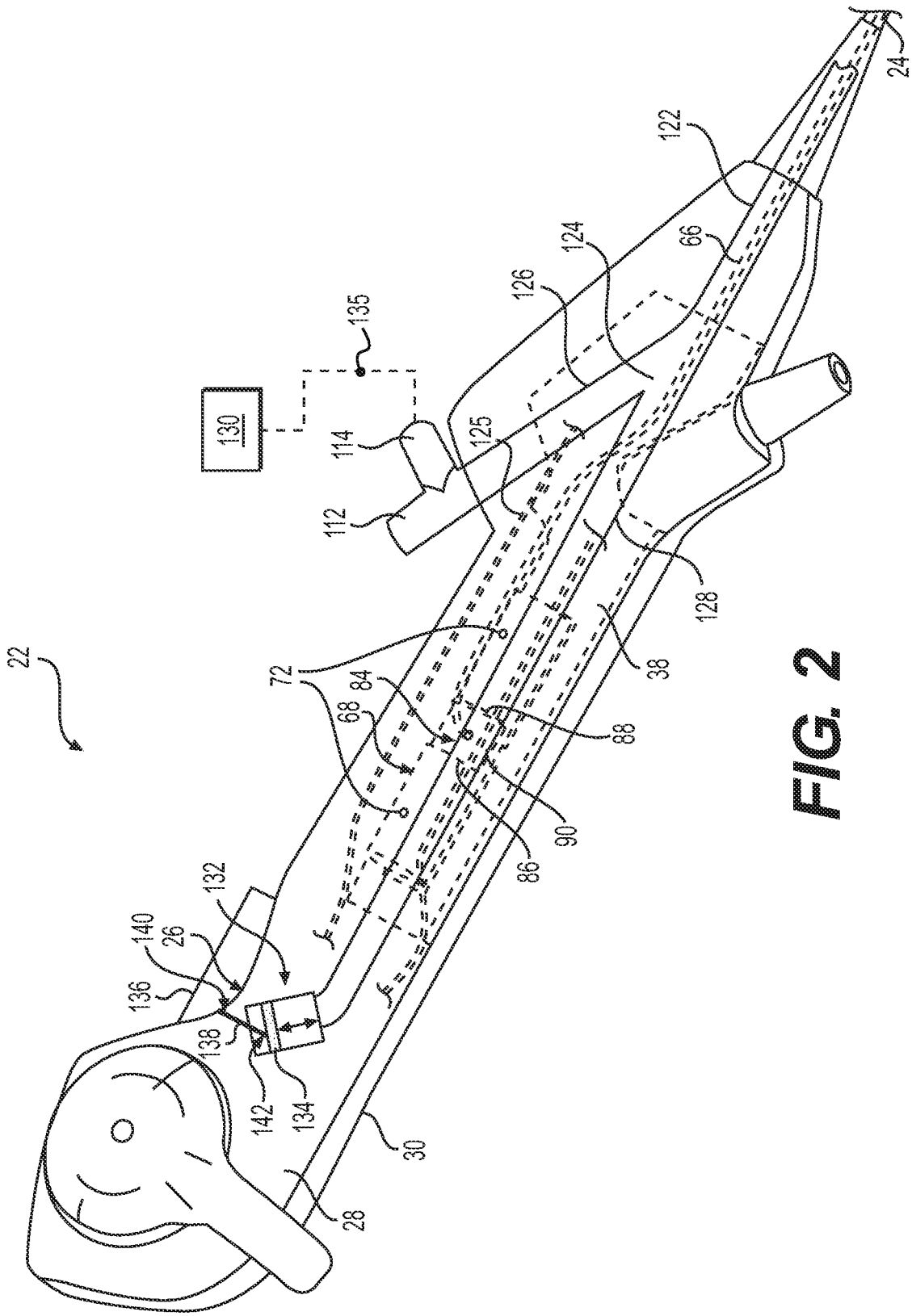
FIG. 2 is a perspective view of an exemplary handle assembly in accordance with aspects of the present disclosure.

FIG. 2 shows an exemplary embodiment of handle assembly 22. Handle assembly 22 may include a handle housing 26. Handle housing 26 may include two half-portions 28 and 30 joined together by appropriate fasteners. For example, half-portions 28 and 30 may be joined together by removable fasteners, such as screws and pins, or by non-removable fastening techniques, such as heat bonding or adhering with an adhesive.

Referring back to FIG. 1, medical device 12 may also include an imaging assembly 32. Imaging assembly 32 may include an image sensor 34 at a distal end of tubular member 24. For example, image sensor 34 may be at a distalmost tip of tubular member 24. Image sensor 34 may be at least partially mounted within, or embedded within, the distal end of tubular member 24. It is also contemplated that tubular member 24 may have a distal end cap (not shown), and image sensor 34 may be positioned therein. Image sensor 34 may view an area distal to the distal end of tubular member 24.

Image sensor 34 may be any suitable type of image sensor configured to capture images and/or full-motion video images in digital or any other suitable format. Image sensor 34 may include, for example, a charged couple device ("CCD") or a complementary metal oxide semiconductor ("CMOS") image sensor. An image sensor connector 36, which may include, for example, one or more electrical wires or cables extending through an interior of tubular member 24, may connect the image sensor 34 to a printed circuit board ("PCB") 38 mounted within an interior of handle housing 26. PCB 38 may mechanically support and/or electrically connect electronic components using conductive tracks, pads, and other features. It is contemplated that electronic components like capacitors, resistors, or active devices, may be mounted on PCB 38.

PCB 38 may be secured within handle housing 26 by any suitable attachment. For example, PCB 38 may be fastened by appropriate fasteners (not shown), such as screws and pins, and/or by fastening techniques, such as heat bonding and adhesive bonding. PCB 38 may be attached to a suitable ground to discharge errant electrical surges, so such surges are less likely to damage components in electronic communication with PCB 38. It is also contemplated that PCB 38 may be supported in handle housing 26 by one or more structures (not shown), such as ridges or protrusions, extending toward PCB 38 from an interior surface of handle housing 26.

Imaging assembly 32 may also include an imaging card or circuit board 44, shown in FIG. 1. Imaging card 44 may be housed in interface box 14. Imaging card 44 may include, for example, any suitable circuit board configured to drive the capture of image data with image sensor 34. For example, imaging card 44 may include appropriate circuitry and memory to calibrate captured image data from image sensor 34, deserialize the captured image data, perform known algorithms, such as demosaicing, gain control, and white balance, and/or any other suitable functions, to produce a quality color image. The gain control may be implemented by imaging card 44 by adjusting gains applied to the image data from image sensor 34.

Alternatively, imaging card 44 may include appropriate circuitry and memory to calibrate captured image data from image sensor 34, decode or deserialize the captured image data, and format the data for transmission to computer 16. Computer 16 may perform known algorithms, such as demosaicing, gain control, and white balance, and/or any other suitable functions, to produce a quality color image. The gain control may be implemented by computer 16 by adjusting gains applied to the image data from image sensor 34.

Imaging card 44 may also include isolation circuitry to prevent undesired radio frequency susceptibility, emissions and interference, as well as undesired leakage currents in the event of an electrical failure. Interface box 14 and imaging card 44 may be coupled to handle assembly 22 and PCB 38 by distal connector 18. Imaging card 44 may receive image data from image sensor 34 through image sensor connector 36, PCB 38, and distal connector 18.

Distal connector 18 may operably connect handle assembly 22 to interface box 14. Distal connector 18 may provide an electronic signal pathway for signals between interface box 14 and imaging assembly 32. For example, distal connector 18 may provide a communication pathway for signals between imaging card 44 and PCB 38. Distal connector 18 may also provide power from interface box 14 to medical device 12. Distal connector 18 may include a scope cable. The scope cable may include one or more electrical wires, and/or an electrical conduit. Distal connector 18 may also include a suitable structure on its proximal end, such as a proximal plug 46, configured to readily attach to and detach from interface box 14, by entering into and exiting from a distal port 48 of interface box 14. For example, proximal plug 46 may include a point-to-point adapter, splice, multi-port adapter, and/or a snap-fit connection. Distal connector 18 may also include a distal plug (not shown), configured to readily attached to and detach from a proximal port (not shown) on medical device 12. Accordingly, distal connector 18 may operably link medical device 12 to interface box 14 when performing a procedure utilizing medical device 12. Distal connector 18 may readily detach medical device 12 from interface box 14 when the procedure is completed, and medical device 12 is to be disposed of, or sterilized for subsequent use. It is also contemplated that in some embodiments, distal connector 18 may be fixedly attached to at least one of interface box 14 and medical device 12.

Imaging assembly 32 may also include one or more components forming computer 16. Computer 16 may include a smartphone, tablet computer, laptop computer, desktop computer, and/or any other suitable computing device. Computer 16 may include a display 50, as well as other electronic components (not shown), such as a central processing unit, memory, video and graphics cards, wireless and wired networking devices, audio devices, one or more input/output ports, a power supply, and/or any other suitable computer features. In other embodiments, computer 16 may be replaced by a screen or monitor with less of, or without, the computing power of computer 16.

In one embodiment, display 50 may include a touch screen for displaying image data, and for receiving inputs or commands from a user. User interaction may be directed toward aspects of image capture, video capture, brightness control, mode controls, narrow band imaging toggle, and/or any other controls that may be part of a typical ureteroscopy procedure. Display 50 may be mounted on a structure (not shown), such as an existing tower using an adjustable arm, a subject bed, a boom system, on a monitor mount on a stand, and/or on a separate rolling or stationary stand.

Computer 16 may be coupled to interface box 14, and imaging card 44, by proximal connector 20. Computer 16 may receive image data from imaging card 44 via proximal connector 20. Computer 16 may include imaging electronics configured to process and/or transfer the image data, display the image data on display 50 for viewing by a user, and send signals to imaging card 44 for controlling electronic components of PCB 38 and/or image sensor 34. For example, imaging card 44 may calibrate captured image data based on commands from computer 16.

Proximal connector 20 may operably connect interface box 14 to computer 16. Proximal connector 20 may provide an electronic signal pathway for signals between computer 16 and interface box 14. For example, proximal connector 20 may provide a communication pathway for signals between computer 16 and imaging card 44. Proximal connector 20 may also provide power from a power supply, such as a battery or power adapter of computer 16, to imaging card 44. Proximal connector 20 may be a cable, such as a universal serial bus ("USB") cable, and may include, for example, one or more electrical wires, and/or an electrical conduit. Proximal connector 20 may also include a suitable structure on each end, such as a proximal plug 52 and a distal plug 54. The proximal plug 52 may be configured to readily attach to and detach from computer 16, by entering and exiting from a port 56 of computer 16. The distal plug 54 may be configured to readily attach to and detach from interface box 14, by entering and exiting from a proximal port 58 of interface box 14. For example, proximal and distal plugs 52 and 54 may include point-to-point adapters, splices, multi-port adapters, snap-fit connections, and/or USB plugs. Accordingly, proximal connector 20 may operably link computer 16 to interface box 14 when performing a procedure, and may readily detach from interface box 14 and/or computer 16 when the procedure is completed.

The ease of attaching and detaching computer 16, interface box 14, and medical device 12, with proximal and distal connectors 18 and 20, may provide a user with the ability to easily switch out any one of, or any combination of components. This may be beneficial when, for example, one or more of the components malfunctions. The malfunctioning components may be unplugged, and replaced with functioning components. Furthermore, it is contemplated that multiple types of medical devices may be used with a single computer by, for example, plugging in an appropriate interface box to ensure compatibility between the computer and whatever medical device is being used. When the medical device is switched for another, a different interface box may be connected between the computer and the medical device. Another potential benefit is that if the computer and/or the medical device is upgraded, the interface box can be modified to ensure continued compatibility between the two components.

Medical device 12 may also include an illumination assembly 60. As shown in FIG. 1, illumination assembly 60 may include an illumination unit 62, such as a light-emitting diode ("LED"), an illumination card or circuit board 64, at least one illumination fiber 66, and a heat sink 68. LED 62 may be mounted on PCB 38 in the interior of handle housing 26. Exemplary embodiments are shown in FIGS. 1 and 2. LED 62 may be mounted on conductive tracks or pads on PCB 38. LED 62 may emit light upon receipt of an appropriate power supply. The power supply may come from computer 16, for example from a battery or power adapter of computer 16, via connectors 18 and 20 and interface box 14. LED 62 may include, for example, a LUXEON Z LED. Any other suitable LED may be used.

Illumination fiber 66, shown in FIG. 2, may be coupled at a proximal end to LED 62, and at a distal end to the distal end of tubular member 24. Illumination fiber 66 may transmit the light emitted by LED 62 to the distal end of tubular member 24, where the light may be emitted from the distal tip of illumination fiber 66 to areas around the distal end of tubular member 24. Illumination fiber 66 may include an optical fiber made of plastic, glass, or any other suitable light transmissive material.

Illumination card 64 may be housed in interface box 14, as shown in FIG. 1. Illumination card 64 may help drive and/or control operation of LED 62. For example, illumination card 64 may help control the light output of LED 62. Distal connector 18 may provide electronic signaling pathways for illumination card 64 to control light output from LED 62. The electronic signaling pathways may be similar to the ones linking imaging card 44 to PCB 38. Distal connector 18 may also provide an electrical conduit for power to be supplied to LED 62 from illumination card 64. Proximal connector 20 may provide a communication pathway for signals between computer 16 and illumination card 64. Proximal connector 20 may also provide power from the power supply of computer 16 to illumination card 64, for use by LED 62.

Because LED 62 is in handle housing 26, and not, for example, in interface box 14 or computer 16, illumination fibers may be omitted from proximal and distal connectors 18 and 20. Thus, specialized connectors with illumination fibers therein are not required for medical system 10. For example, conventional USB and scope cables may be used. Further, because LED 62 is in handle housing 26 rather than in computer 16, computers that do not include LEDs therein may be used in medical system 10. Furthermore, because LED 62 is not, for example, at the distal end of tubular member 24, the diameter of the distal end need not be enlarged to fit LED 62 and any heat sinks necessary to cool LED 62.

It is contemplated that one or more actuators or buttons (not shown) may be disposed on handle assembly 12, for controlling operation of LED 62. Additionally or alternatively, one or more actuators or buttons may be disposed on computer 16, for controlling operation of LED 62. In one embodiment, gain control for imaging may be implemented by adjusting the intensity of LED 62, and adjusting the gains applied to the signals by image sensor 34. That gain control may be implemented by computer 16, imaging card 44 and illumination card 64, and/or electronic components on PCB 38.

LED 62 may generate heat when activated. The heat may be dissipated from LED 62 by heat sink 68. Heat sink 68 may be mounted on PCB 38. Heat sink 68 may be mounted using any suitable attachment. For example, heat sink 68 may be fastened to PCB 38 by appropriate fasteners 70, such as screws and pins, and/or by fastening techniques, such as heat bonding and adhesive bonding. When mounted on PCB 38, a bottom surface of heat sink 68 may contact one or more surfaces of LED 62. Heat generated by LED 62 may transfer into heat sink 68, and heat sink 68 may dissipate the heat.

Heat sink 68 may remain out of contact with handle housing 26. This may ensure that heat dissipated from heat sink 68 may not directly heat a portion of handle housing 26, thereby possibly damaging handle housing 26 or making it uncomfortable for a user to grip handle housing 26. Heat sink 68 may include one or more mounting holes 72 for receiving fasteners 70 to fasten heat sink 68 to PCB 38. Mounting holes 72 may extend in a direction substantially transverse to a longitudinal axis of heat sink 68.

It is also contemplated that a layer of material may be provided between surfaces of heat sink 68 and LED 62 prevent one from damaging the other by rubbing or impact, and/or to ensure close contact between heat sink 68 and LED 62, while still allowing heat to be transmitted from LED 62 to heat sink 68 through the layer of material. For example, the layer of material may include thermal adhesive or thermal grease.

Handle assembly 22 may also include a steering mechanism 116 (FIGS. 1 and 2). Steering mechanism 116 may be configured to control the steering and deflection of tubular member 24. Steering mechanism 116 may include a first actuator 118 and a second actuator 120 configured to control deflection of a distal portion of tubular member 24 between a substantially linear configuration and a variety of curved, angled, or bent configurations, in a variety of different directions relative to a longitudinal axis 74 of tubular member 24. For example, actuating first actuator 118 in opposing directions may cause the distal portion of tubular member 24 to deflect in opposing directions along a first plane. Actuating second actuator 120 in opposing directions may cause the distal portion of tubular member 24 to deflect in opposing directions along a second plane different than the first plane. Accordingly, steering mechanism 116 may provide four-way steering of the distal portion of tubular member 24. The ability to steer allows the user to achieve visualization of almost any internal area in the subject's body.

Steering mechanism 116 may include one or more control members (FIG. 2) including, for example, one or more control members 125. Control members 125 may be coupled to first and second actuators 118 and 120, and may extend through handle housing 26 and through tubular member 24. Furthermore, control members 125 may each be coupled to tubular member 24 at or near the distal tip of tubular member 24. Control members 125 may be supported by portions of handle housing 26, such that portions of control members 125 are curved away from or otherwise spaced from heat sink 68. First and second actuators 118 and 120 may control deflection of a distal portion of tubular member 24 by selectively extending and retracting control members 125. Control members 125 may include four Bowden cables. One pair of cables may be selectively pushed and pulled by moving first actuator 118 proximally and distally to deflect the distal portion of tubular member 24 in two directions along a first plane. The other pair of cables may be selectively pushed and pulled by moving second actuator 120 proximally and distally to deflect the distal portion of tubular member 24 in two directions along a second plane transverse to the first plane.

Handle assembly 22 may also include ports 112 and 114. Ports 112 and 114 may provide access to one or more channels, such as working channel 122 extending through tubular member 24. For example, port 112 and/or port 114 may provide access for one or more medical instruments or tools into one or more channels, including working channel 122 extending through tubular member 24 and out the distal tip of tubular member 24. Additionally or alternatively, port 112 and/or port 114 may provide access into one or more working channels, such as working channel 122, for delivering a suitable fluid, such as a liquid or gas, for irrigation and insufflation purposes, respectively, to and out of the distal tip of tubular member 24. It is also contemplated that port 112 and/or port 114 may be in fluid communication with one or more working channels, such as working channel 122, for withdrawing material from tubular member 24 and/or an area near the distal tip of tubular member 24, using suction. Tubular member 24 may include one or more additional channels for receiving other components, such as image sensor connector 36, and/or illumination fiber 66. Such additional channels may be accessible by separate ports, for example port 112 may be provided in fluid connection with one channel and port 114 may be provided in fluid connection with a separate channel. It is also contemplated that port 112 and/or port 114 may be provided with a one-way valve or septum seal configured to seal the port or prevent leakage of the fluid or other flowable material when one or more medical devices are introduced therein.

Working channel 122 may be positioned downstream of bifurcation 124. Bifurcation may couple branches 126 and 128 to working channel 124. For example, branches 126 and 128 may converge at bifurcation 124 and continue on as working channel 122. Branch 126, as shown in FIG. 2, may be coupled to port 114, which may be, in turn, coupled to a source of sterile irrigation fluid 130. Source 130 may be, for example, a bag or container of saline, water, medicament, cleaning solution, or the like, suspended from an IV pole or other structure and fluidly coupled to port 114. A medical professional may, during the course of a procedure, determine a need for irrigation fluid to be delivered through working channel 122. Accordingly, the medical professional may actuate a valve system 135 such that fluid flowing from source 130 may be delivered through working channel 122. Valve system 135 may include a stock cock and/or a pinch valve to selectively allow irrigation fluid to flow between source 130 and port 114 under the force of gravity. For example, the higher the source 130 is raised (e.g., via a pole or similar structure), the greater the pressure and/or flow rate of the irrigation fluid may pass from source 130 to port 114 and through working channel 122. In some examples, valve system 135 may be a one-way valve so as to prevent backflow of fluid towards source 130.

In order to urge fluid from source 130 through working channel 122, a pressurizer 132 may be positioned within branch 128 and upstream of port 114. For example, the pressurizer 132 may be configured as a miniature pump positioned within the interior of the handle housing 26. As shown in FIG. 2, pressurizer 132 may include a micro-piston pump. Alternatively, pressurizer 132 may include any appropriate pump configuration including, for example, reciprocating pumps and/or rotating pumps such as a peristaltic pump. Pressurizer 132 may include a displaceable member 134 such as a piston or the like. The displaceable member 134 may be moved by manipulation of an actuator 136 (e.g., a trigger) via an appropriate linkage 138. For example, actuator 136 may include a button or other depressible member mechanically coupled to a first end 140 of linkage 138. As such, upon depression of actuator 136, linkage 138 may be similarly depressed. A second end 142 of linkage 138 may be mechanically coupled to displaceable member 134. Accordingly, upon depression of linkage 138 via actuator 136, displaceable member 134 is also depressed thereby actuating pressurizer 132 to create a pressure differential in branch 128. The pressure differential may urge fluid in the working channel 122 distally along the working channel 122 and out through the distal end of tubular member 24. When actuator 136 is released, built-up fluid pressure in branch 128 may urge displacement member 134 to return back towards its original and/or neutral position, which in turn pushes linkage 138 and actuator 136 back towards their undepressed state. In this manner, no additional spring or return force is required to "reset" pressurizer 132 and/or actuator 136.

In use, irrigation fluid may be caused to flow, under the force of gravity, from source 130 to port 114, along branch 126, and then through working channel 122 upon the opening of valve system 135. Once branch 128 is filled with fluid from source 130, fluid from source 130 will generally flow out of working channel 122. If, however, a medical professional determines that the flow of irrigation fluid from source 130 is insufficient to effectively clean or cause a viewing window, port, or lens of medical device 12 to become unobstructed, he or she may depress actuator 136 to actuate pressurizer 132 to drive fluid in branch 128 distally and suck and/or pull additional fluid from source 130 towards and through working channel 122 of tubular member 24. In other words, actuation of actuator 136 may increase the pressure of fluid in branch 128 thereby urging fluid in branch 128 toward bifurcation 124. Once the pressurized fluid in branch 128 reaches bifurcation 124, fluid from source 130 and within branch 126, which is at a lower pressure than the fluid in branch 128, may be drawn towards and urged distally along working channel 122. Accordingly, fluid from source 130 may be delivered at a higher flow rate and/or pressure through working channel 122 upon actuation of actuator 136. When the medical professional determines that the viewing window, port, or lens of medical device 12 has been sufficiently cleared, he/she may remove their finger or hand from actuator 136, thereby allowing built-up pressure in branch 128 to return actuator 136 towards its undepressed state.

Figure 3:
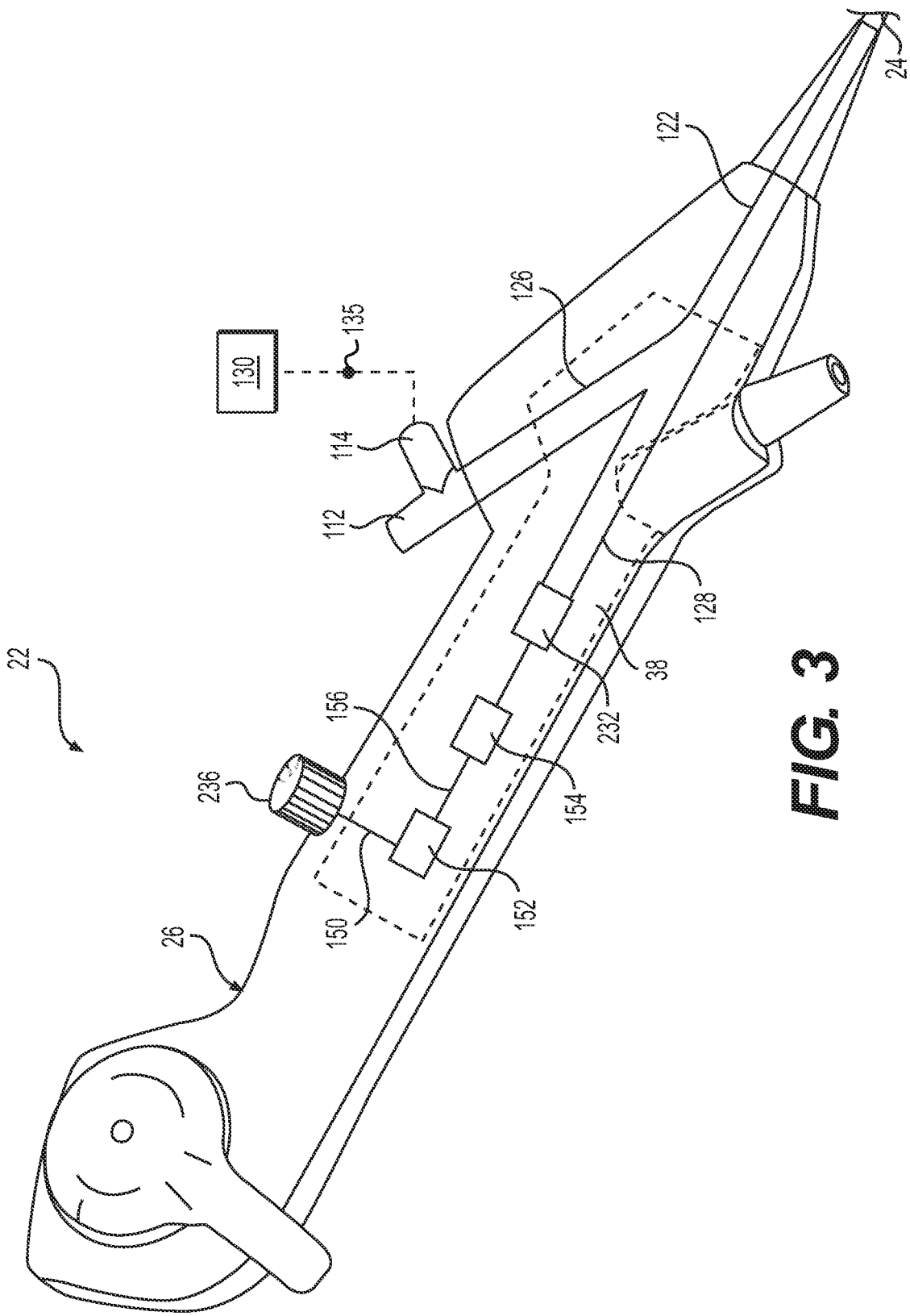
FIG. 3 is a perspective view of an additional exemplary handle assembly in accordance with aspects of the present disclosure.

In an additional example, an alternative pressurizer 232 and actuator 236 may be employed. In such an arrangement, actuator 236 may be configured as a rotatable dial. Indicia on actuator 236 may convey a unit of measurement. For example, a first mark or indicia may indicate a first unit of measurement, where a second mark or indicia may indicate a second unit of measurement. The indicia may correspond to various features of actuation of pressurizer 232. These features may include flow rate, frequency, and/or duration of desired irrigation fluid through working channel 122. A medical professional may turn or otherwise move actuator 236 to select a particular unit of measurement. As shown in FIG. 3, in which certain components are not depicted for clarity, actuator 236 may be coupled to a memory 152 on PCB 38 via a signal conductor 150 for transmitting information therebetween. Such information may include, for example, a flow rate, frequency, and/or duration of desired irrigation fluid through working channel 122. Memory 152 may be a volatile memory for storing programming data. Memory 152 may store commands and/or instructions for actuating pressurizer 232 in the form of executable software and/or programs. For example, upon the selection of a first actuator 236 position by a medical professional, a signal may be transmitted to the memory 152 via signal conductor 150 indicating a first flow rate, frequency, and/or duration of desired irrigation fluid through working channel 122. Additionally, upon the selection of a second actuator 236 position by a medical professional, a signal may be transmitted to the memory 152 via signal conductor 150 indicating a second flow rate, frequency, and/or duration of desired irrigation fluid through working channel 122. In this manner, a medical professional may cause pressurizer 232 to adjust the flow rate, frequency, and/or duration of desired irrigation fluid pumped through working channel 122.

Memory 152 may be coupled with a motor or power source 154 via a signal conductor 156, which in turn, is configured to drive pressurizer 232 to create a pressure differential in branch 128. For example, upon transmission of a signal via signal conductor 150, signal conductor 156 may transmit a corresponding signal to motor 154 to indicate the desired flow rate, frequency, and/or duration of desired irrigation fluid through working channel 122. Once received by the motor 154, the motor may drive pressurizer 232 to pressurize fluid thereby creating a pressure differential in branch 128. The pressure differential may urge fluid in the working channel 122 distally along the working channel 122 and out through the distal end of tubular member 24.

For example, in some embodiments, pressurizer 232 may be a micro-peristaltic pump. In such examples, motor 154 may be a rotor (not shown) having any one or more rollers attached to an external surface thereof. As the rotor rotates, the one or more rollers may compress or pinch a flexible tube (not shown) fluidly coupled to branch 128 and surrounding the rotor thus pressurizing fluid in the tube and forcing the pressurized fluid to be moved along the tube and towards working channel 122. As such, a pressure differential may be formed in branch 128 which may urge fluid in the working channel 122 distally along the working channel 122 and out through the distal end of tubular member 24.

In use, irrigation fluid may be caused to flow, under the force of gravity, from source 130 to port 114, along branch 126, and then through working channel 122 upon the opening of valve system 135. Once branch 128 is filled with fluid from source 130, fluid from source 130 will generally flow out of working channel 122. If, however, a medical professional determines that the flow of irrigation fluid from source 130 is insufficient to effectively clean or cause a viewing window, port, or lens of medical device 12 to become unobstructed, he or she may rotate or otherwise actuate actuator 236 to actuate pressurizer 232 to drive fluid in branch 128 distally and suck and/or pull additional fluid from source 130 towards and through working channel 122 of tubular member 24. In other words, actuation of actuator 236 may increase the pressure of fluid in branch 128 thereby urging fluid in branch 128 toward bifurcation 124. Once the pressurized fluid in branch 128 reaches bifurcation 124, fluid from source 130 and within branch 126, which is at a lower pressure than the fluid in branch 128, may be drawn towards and urged distally along working channel 122. Accordingly, fluid from source 130 may be delivered at a higher flow rate, frequency, and/or duration through working channel 122 upon actuation of actuator 236.

Figure 4:
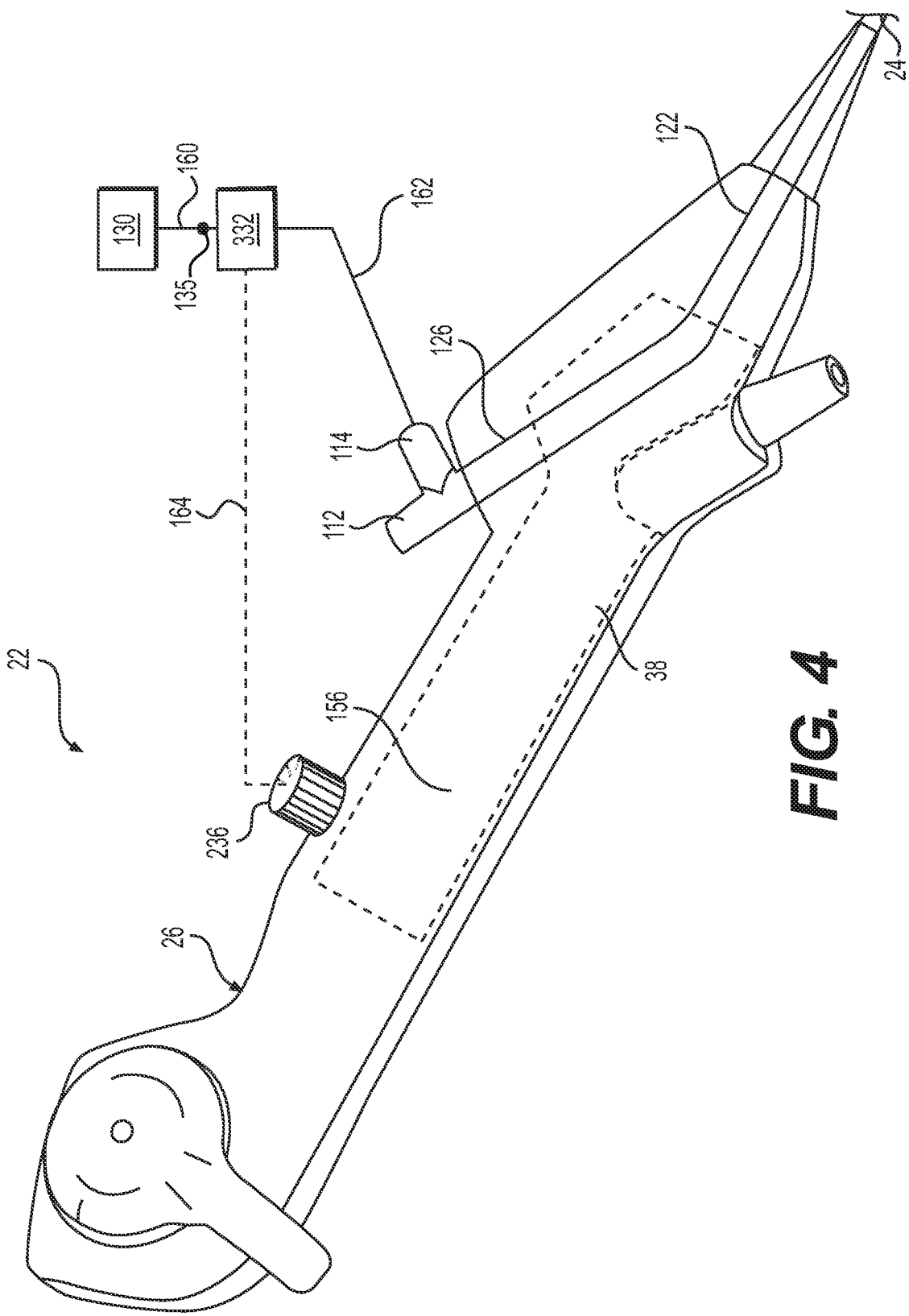
FIG. 4 is a perspective view of another exemplary handle assembly in accordance with aspects of the present disclosure.

In an additional example, pressurizer 332 may be positioned externally of handle assembly 22. For example, as shown in FIG. 4, pressurizer 332 may be coupled to source 130 externally of handle assembly 22 via fluid conductor (e.g., tubing) 160. Additionally, the pressurizer 332 may be coupled to port 114 via fluid conductor 162 (e.g., tubing). Additionally, pressurizer 332 may be coupled to actuator 236 via a signal conductor 164. In an alternative example, however, actuator 236 may be configured to wirelessly communicate with pressurizer 332. Similarly to the example shown in FIG. 3, actuator 236 may be configured as a rotatable dial. Indicia on the actuator may convey a unit of measurement. For example, a first mark or indicia may indicate a first unit of measurement, where a second mark or indicia may indicate a second unit of measurement. The indicia may correspond to various features of actuation of pressurizer 332. These features may include flow rate, frequency, and/or duration of desired irrigation fluid through working channel 122. A medical professional may turn or otherwise move actuator 236 to select a particular unit of measurement. Once selected, actuator 236 may communicate the desired selection with pressurizer 332 via signal conductor 164 and/or wirelessly to drive pressurizer 332 to pressurize fluid from source 130, thereby creating urging fluid in the working channel 122 distally along the working channel 122 and out through the distal end of tubular member 24.

During a procedure, a medical professional may determine that a viewing window, port, or lens of medical device 12 has become obstructed with blood, tissue, fluids, and other materials within the body, or may become fogged over with condensation such that it prevents a medical professional from clearly viewing the body lumen and/or a medical tool extended through the medical device 12. Accordingly, the medical professional may actuate actuator 236 so as to drive pressurizer 332 such that fluid flowing from source 130 may be delivered through working channel 122.

The examples disclosed herein include numerous features. For instance, in order to clean a viewing window, port, or lens of medical device 12, a medical professional no longer is required to remove the medical device 12 from the patient and manually wipe or otherwise remove debris or condensation. Accordingly, the medical procedure may be performed increasingly efficiently and without losing a particular positioning of the medical device 12 within the patient. Additionally, and in regard to the examples depicted in FIGS. 2 and 3, positioning of the pressurizer 132 or 232 within the handle assembly 22 affords the medical professional with more working space and less interface from additionally coupled external pressurizers or other equipment. These arrangements also allow a medical professional to maintain both of his or her hands on the medical device 12 to actuate the pressurizer 132, 232 and/or 332 and prevent any misalignment or lost positioning of the medical device 12 that may be experienced when removing one of the medical professional's hands. Also, providing the ability for the medical professional to operate the pressurizer 132, 232, and/or 332 from the handle assembly 22 of the medical device, reduces the need for additional assistants to operate a pressurizer, thereby lowering health care costs, preventing miscommunication, and improving procedural efficiency.

Any aspect set forth in any embodiment may be used with any other embodiment set forth herein. Every device and apparatus set forth herein may be used in any suitable medical procedure, may be advanced through any suitable body lumen and body cavity, and may be used for treatment of any suitable body portion. For example, the apparatuses and methods described herein may be used in any natural body lumen or tract, including those accessed orally, vaginally, or rectally.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the disclosure is not to be considered as limited by the foregoing description.

I claim:

1. A method of using a medical device to deliver irrigation fluid, comprising:
   delivering irrigation fluid from a source of irrigation fluid through an irrigation port in a handle housing of the medical device, the handle housing coupled to a proximal end of an insertion portion of the medical device, wherein the handle housing includes a first branch and a second branch within the handle housing such that the irrigation port and the first branch and the second branch are in fluid communication with a channel via a bifurcation within the handle housing, and such that irrigation fluid is delivered from the source of irrigation fluid, through the first branch, and into the channel; and
   delivering additional irrigation fluid from the source of irrigation fluid through the irrigation port in the handle housing such that irrigation fluid is delivered from the source of irrigation fluid through the first branch and into the second branch via the bifurcation, wherein the irrigation fluid in the second branch provides a supplemental reservoir of irrigation fluid.

2. The method of claim 1, further comprising:
   manipulating an actuator coupled to a portion of the handle housing of the medical device to actuate a pressurizer positioned within an interior of the handle housing to act on irrigation fluid contained in the second branch such that irrigation fluid from within the second branch is urged distally through the channel.

3. The method of claim 1, wherein the channel includes a channel longitudinal axis, wherein the second branch includes a second branch longitudinal axis that is coaxial with the channel longitudinal axis, and wherein the first branch includes a first branch longitudinal axis that extends at a non-zero angle relative to the channel longitudinal axis.

4. The method of claim 2, wherein the actuator is coupled to a proximal portion of the handle housing, and wherein the actuator includes at least one of a depressible trigger or a rotatable dial on the proximal portion of the handle housing.

5. The method of claim 2, wherein the pressurizer is within the handle housing and is configured to act directly on the irrigation fluid in the second branch to urge the irrigation fluid distally through the channel.

6. The method of claim 2, wherein the irrigation port extends from the handle housing, wherein the irrigation port is distal to the actuator on the handle housing, and wherein the delivering of the irrigation fluid from the source of irrigation fluid through the irrigation port includes the irrigation fluid flowing under the force of gravity.

7. The method of claim 5, wherein the pressurizer is positioned upstream of the bifurcation, and wherein the pressurizer is coupled to the second branch at a proximal-most portion of the second branch within the handle housing.

8. The method of claim 5, wherein the pressurizer includes a displacement member, and wherein the medical device further includes a direct physical linkage between the actuator and the displacement member.

9. A method of using a medical device to deliver irrigation fluid, comprising:
   delivering irrigation fluid from a source of irrigation fluid through an irrigation port in a handle housing of the medical device, the handle housing coupled to a proximal end of an insertion portion of the medical device, wherein the handle housing includes a first branch and a second branch within the handle housing such that the irrigation port and the first branch and the second branch are in fluid communication with a channel via a bifurcation within the handle housing, and such that irrigation fluid is delivered from the source of irrigation fluid, through the first branch, and into the channel;
   delivering additional irrigation fluid from the source of irrigation fluid through the irrigation port in the handle housing such that irrigation fluid is delivered from the source of irrigation fluid through the first branch and into the second branch via the bifurcation, wherein the irrigation fluid in the second branch provides a supplemental reservoir of irrigation fluid; and manipulating an actuator of the medical device to actuate a pressurizer to act on irrigation fluid contained in the second branch such that irrigation fluid from within the second branch is urged distally through the channel.

10. The method of claim 9, wherein the actuator is coupled to a proximal portion of the handle housing, and wherein the actuator includes at least one of a depressible trigger or a rotatable dial on the proximal portion of the handle housing.

11. The method of claim 9, wherein the pressurizer is positioned upstream of the bifurcation, wherein the pressurizer is within the handle housing and is coupled to the second branch at a proximalmost portion of the second branch within the handle housing, and wherein the pressurizer is configured to act directly on the irrigation fluid in the second branch to urge the irrigation fluid distally through the channel.

12. The method of claim 9, wherein the irrigation port extends from the handle housing, wherein the irrigation port is distal to the actuator on the handle housing, and wherein the delivering of the irrigation fluid from the source of irrigation fluid through the irrigation port includes the irrigation fluid flowing under the force of gravity.

13. The method of claim 9, wherein the channel includes a channel longitudinal axis, wherein the second branch includes a second branch longitudinal axis that is coaxial with the channel longitudinal axis, and wherein the first branch includes a first branch longitudinal axis that extends at a non-zero angle relative to the channel longitudinal axis.

14. The method of claim 11, wherein the pressurizer includes a displacement member, and wherein the medical device further includes a direct physical linkage between the actuator and the displacement member.

15. A method of using a medical device to deliver irrigation fluid, comprising:
delivering irrigation fluid from a source of irrigation fluid via the force of gravity through an irrigation port in a handle housing of the medical device, the handle housing coupled to a proximal end of an insertion portion of the medical device, wherein the handle housing includes a first branch and a second branch within the handle housing such that the irrigation port and the first branch and the second branch are in fluid communication with a channel via a bifurcation within the handle housing, and such that irrigation fluid is delivered from the source of irrigation fluid, through the first branch, and into the channel; and
delivering additional irrigation fluid from the source of irrigation fluid via the force of gravity through the irrigation port in the handle housing such that irrigation fluid is delivered from the source of irrigation fluid through the first branch and into the second branch via the bifurcation, wherein the irrigation fluid in the second branch provides a supplemental reservoir of irrigation fluid.

16. The method of claim 15, wherein the channel includes a channel longitudinal axis, wherein the second branch includes a second branch longitudinal axis that is coaxial with the channel longitudinal axis, and wherein the first branch includes a first branch longitudinal axis that extends at a non-zero angle relative to the channel longitudinal axis.

17. The method of claim 15, further comprising:
manipulating an actuator of the medical device to actuate a pressurizer to act on irrigation fluid contained in the second branch, such that irrigation fluid from within the second branch is urged distally through the channel.

18. The method of claim 17, wherein the actuator is coupled to a proximal portion of the handle housing, and wherein the actuator includes at least one of a depressible trigger or a rotatable dial on the proximal portion of the handle housing.

19. The method of claim 17, wherein the pressurizer is positioned upstream of the bifurcation, wherein the pressurizer is within the handle housing and is coupled to the second branch at a proximalmost portion of the second branch within the handle housing, and wherein the pressurizer is configured to act directly on the irrigation fluid in the second branch to urge the irrigation fluid distally through the channel.

20. The method of claim 19, wherein the pressurizer includes a displacement member, and wherein the medical device further includes a direct physical linkage between the actuator and the displacement member.

\* \* \* \* \*